(12) United States Patent
Nesbit

(10) Patent No.: US 6,221,403 B1
(45) Date of Patent: Apr. 24, 2001

(54) TOPICAL COMPOSITION

(75) Inventor: Michael Robert Nesbit, Louth (GB)

(73) Assignee: Seton Healthcare Group PLC, Lancashire (GB)

( * ) Notice: Subject to any disclaimer, the term of this patent is extended or adjusted under 35 U.S.C. 154(b) by 0 days.

(21) Appl. No.: 08/382,056

(22) PCT Filed: Aug. 5, 1993

(86) PCT No.: PCT/GB93/01662

§ 371 Date: Feb. 8, 1995

§ 102(e) Date: Feb. 8, 1995

(87) PCT Pub. No.: WO94/03190

PCT Pub. Date: Feb. 17, 1994

(51) Int. Cl.$^7$ ............... A61K 33/30; A61K 7/40; A61K 7/48; A61K 9/06

(52) U.S. Cl. ............ 424/642; 424/641; 424/647; 424/648; 424/402; 424/404; 424/443; 424/444; 424/445; 424/446; 424/447; 424/449; 424/DIG. 13; 424/485; 424/488; 514/777; 514/780; 514/782; 514/785; 514/786; 514/789; 514/827; 514/828; 514/829; 514/830; 514/848; 514/859

(58) Field of Search ............ 424/641, 642, 424/647, 648, 402, 404, 443–447, 449, 485, 488, DIG. 13; 514/777, 780, 782, 785, 786, 789, 827–830, 848, 859, 861–865, 887, 969, 970, 975

(56) References Cited

U.S. PATENT DOCUMENTS

| 3,803,300 | * | 4/1974 | Pospischil | 424/443 |
| 4,512,978 | | 4/1985 | Inwood | 424/145 |
| 4,678,664 | * | 7/1987 | Schmolka | 424/65 |
| 4,816,254 | | 3/1989 | Moss | 514/494 |
| 4,909,243 | | 3/1990 | Frank et al. | 128/156 |
| 5,948,416 | | 9/1999 | Wagner et al. | 424/401 |

FOREIGN PATENT DOCUMENTS

| 1128170 | | 9/1968 | (GB) . |
| 2233227A | | 1/1991 | (GB) . |
| 57-171907 | * | 10/1982 | (JP) . |

OTHER PUBLICATIONS

Remington's Pharmaceutical Sciences, 18th ed., Mack Printing Co., PA, 1990, pp. 762–763, 1602–1604, 1613, 1990.*

Derwent Abstract Accession No. 82–03408J, abstracting JP 57–171907, Oct. 22, 1982.*

* cited by examiner

Primary Examiner—John Pak
(74) Attorney, Agent, or Firm—Duane, Morris & Heckscher LLP

(57) ABSTRACT

A topical composition for impregnating a bandage comprises zinc oxide in a stable oil in water emulsion. The emulsion comprises one or more fats or oils, one or more emulsifying agents, at least one water soluble gum and water. No preservative is required.

12 Claims, No Drawings

TOPICAL COMPOSITION

This application is a 371 of PCT/GB93/01662, filed on Aug. 5, 1993.

This invention relates to a topical composition comprising zinc. oxide particularly, but not exclusively for impregnating a bandage.

Bandages impregnated with pastes containing zinc oxide are commonly used for the treatment of skin complaints such as leg ulcers, varicose eczemas and chronic dermatitis. These known pastes are not sufficiently emulsified and are therefore unstable, particularly when subjected to sterilisation processes such as heating and irradiation. As these known pastes cannot be properly sterilised it is conventional to include "preservatives" which include antibacterial and antiviral agents, such as alkyl p-hydroxybenzoates, in order to irradicate any bacteria or viruses that are not removed by sterilisation. These preservatives cause hyposensitivity when the bandage comprising the paste is applied to the wound.

The present invention has been made from a consideration of this problem.

According to the present, invention there is provided a topical composition for impregnating a bandage comprising zinc oxide in a stable emulsion comprising at least one fat and/or oil, at least one emulsifying agent, at least one water soluble viscosity improver and water in the absence of a preservative.

The stable emulsions of the compositions of the present invention eliminate the need for a preservative. Thus topical zinc oxide containing compositions can be made which do not suffer from the drawback of sensitivity.

The compositions of the invention are primarily intended for impregnating bandages for use in the treatment of skin diseases.

The zinc oxide is the active agent. The composition preferably comprises from 0.5% to 40.0% wt of zinc oxide and more preferably substantially 15% wt of zinc oxide. The composition may comprise additional active ingredients such as calamine, icthammol, clioquinol and coal tar. The composition preferably comprises from 0 to 40% wt of additional actives.

In a preferred embodiment of the invention the fats and/or oils comprise fractionated coconut oil and/or synthetic spermaceti, combinations of cetyl alcohol; stearyl alcohol; other alcohols ($C_8$ to $C_{24}$); triglyceride oils or fats; esters such as cetyl palmitate, myristyl myristate; liquid and solid paraffins or other commonly used cosmetic fats and oils The fats and/or oil form an oil in water emulsion. The composition preferably comprises from 0.2 to 45% wt fat and/or oil and more preferably from 2 to 16% wt fat and/or oil.

The emulsifying agent is preferably polyethoxylated. Preferred examples include tween 80 polysorbate 20, 21, 40, 60, 61, 65, 81, 85, 120 and other polyoxyethylene adducts of sorbitan esters; fatty acids; fatty alcohols; lanolin; lanolin alcohols; castor oil (natural or hydrogenated) or alkylbenzenes. The emulsifying agent has a high HLB and emulsifies the fat and/or oils into the oil in water emulsion. The composition preferably comprises from 0.3 to 10% wt and still more preferably from 0.5% to 2% wt of emulsifying agent.

The water soluble viscosity improver increases the viscosity of the aqueous phase for stabilisation. One preferred material is xantham gum. The composition preferably comprises from 0.5 to 4.0% of viscosity improver and more preferably from 0.05 to 1.2%.

In a preferred embodiment of the invention the compositions preferably comprise the following ingredients either alone or in combination: at least one low HLB emulsifying agent to emulsify the fats and/or oils, at least one inorganic suspending agent in order to suspend the zinc oxide and improve the stability of the composition and glycerol which acts as a humectant in order to improve the water retention of the composition and to provide emollient properties to the skin.

In order that the present invention may be more readily understood a specific embodiment thereof will now be described with reference to the following example:

EXAMPLE 1

A topical composition in accordance with the present invention was made according to the following formula:

|  | % w/w |
|---|---|
| Purified Water Ph Eur | 49.9 |
| Glycerol Ph Eur | 30.0 |
| Zinc Oxide Ph Eur | 15.0 |
| Fractionated Coconut Oil (Miglyol 812) | 2.0 |
| Aluminium Magnesium Silicate BP (Veegum F) | 1.0 |
| Xanthan Gum USNF (Keltrol F) | 0.8 |
| Polysorbate 80 Ph Eur (Tween 80) | 0.5 |
| Synthetic Spermaceti USNF (Crodamol SS) | 0.5 |
| Sorbitan Mono-oleate BP (Span 80) | 0.3 |

The said formula of Example 1 was made in the following manner:

|  | Per 100 Kg of Batch |
|---|---|
| Part A |  |
| Purified Water Ph Eur | 49.9 Kg |
| Veegum F | 1.0 Kg |
| Tween 80 | 500 g |
| Glycerol Ph Eur | 30 Kg |
| Zinc Oxide | 15 Kg |
| Keltrol F | 800 Kg |
| Part B |  |
| Miglyol 812 | 2.0 Kg |
| Crodamol SS | 500 g |
| Span 80 | 300 g |

The Veegum F was added to the water of the Part A mixture and mixed with high shear agitation, whilst heating to 60° C. The other ingredients of Part A were then added and mixed with high shear agitation at 60° C. The Part B mixture was mixed in a separate small vessel and heated to 60° C. A 10 liter portion of Part A was slowly added to the Part B mixture with brisk stirring. The Part A/B mixture was then added to the remainer of the Part A mixture and mixed with agitation. The vessel used for the A/B mixture was rinsed out with portions of the batch. The batch was periodically mixed with agitation whilst cooling, until the viscosity increased and the batch was then cooled to room temperature with periodic stirring. The batch was re-mixed with high shear agitation, prior to assembly.

The composition of Example 1 was stable when subjected to 120° C. for 15 minutes. The composition was also stable when subjected to gamma irradiation.

The formulation of Example 1 therefore provides a stable zinc oxide containing emulsion which may be subjected to conventional sterilisation techniques.

It is to be understood that the example described above is by way of illustration only. Many modifications and variations are possible.

What is claimed is:

1. A sterilization stable topical paste for impregnating a bandage comprising zinc oxide in a stable emulsion, comprising from 0.5% to 40.0% wt. of zinc oxide, from 0.2 to 45% wt. of at least one fat and/or oil, wherein the fat and/or oil comprises any of the following: fractionated coconut oil and/or synthetic spermaceti; combinations of cetyl alcohol, stearyl alcohol, and $C_8$ to $C_{24}$ alcohols; triglyceride oils or fats; liquid and solid paraffins, from 0.3 to 10% wt. of at least one polyethoxylated emulsifying agent, from 0.5 to 4.0% wt. of at least one water soluble gum which elevates the viscosity of the paste, and water, in the absence of a preservative, wherein said composition is stable when heated to 120° C. for 15 minutes, or alternatively, when subjected to gamma irradiation.

2. A topical paste as claimed in claim 1, wherein the composition further comprises calamine.

3. A topical paste as claimed in claim 2, wherein the paste contains up to 40% wt of calamine.

4. A topical paste as claimed in claim 1, wherein the paste contains from 2 to 16% wt of said fat and/or oil.

5. A topical paste as claimed in claim 1, wherein the emulsifying agent includes any of the following:

a polyethoxylated emulsifier, polyoxyethylene adducts of sorbitan esters, fatty acids, fatty alcohols, lanolin, and alkylbenzenes.

6. A topical paste as claimed in claim 1, wherein the paste contains from 0.5% to 2% wt of said emulsifying agent.

7. A topical paste as claimed in claim 1, wherein the water soluble gum comprises xantham gum.

8. A topical paste as claimed in claim 1, wherein the paste contains from 0.05% to 1.2% wt of said water soluble gum.

9. A topical paste as claimed in claim 1, wherein the paste further comprises at least one inorganic suspending agent.

10. A topical paste as claimed in claim 1, wherein the composition further comprises glycerol.

11. A bandage impregnated by the topical paste of claim 1.

12. A sterilization stable topical paste for impregnating a bandage comprising zinc oxide in a stable emulsion, comprising from 0.5% to 40.0% wt. of zinc oxide, from 0.2 to 45% wt. of at least one fat and/or oil, wherein the fat and/or oil comprises at least one ester selected from the group consisting of cetyl palmitate and myristyl myrisate, from 0.3 to 10% wt. of at least one polyethoxylated emulsifying agent, from 0.5 to 4.0% wt. of at least one water soluble gum which elevates the viscosity of the paste, and water, in the absence of a preservative, wherein said composition is stable when heated to 120° C. for 15 minutes, or alternatively, when subjected to gamma irradiation.

* * * * *